United States Patent
Régnier et al.

(10) Patent No.: US 11,771,889 B2
(45) Date of Patent: *Oct. 3, 2023

(54) IMPLANTABLE DETECTION/STIMULATION MULTIPOLOR MICROLEAD

(71) Applicant: SORIN CRM S.A.S., Clamart (FR)

(72) Inventors: Willy Régnier, Longjumeau (FR); Jean-François Ollivier, Villiers le Bacle (FR); Philippe D'Hiver, Chatillon (FR); Nicolas Shan, Antony (FR)

(73) Assignee: SORIN CRM S.A.S., Clamart (FR)

( * ) Notice: Subject to any disclaimer, the term of this patent is extended or adjusted under 35 U.S.C. 154(b) by 487 days.

This patent is subject to a terminal disclaimer.

(21) Appl. No.: 16/667,222

(22) Filed: Oct. 29, 2019

(65) Prior Publication Data

US 2020/0061367 A1    Feb. 27, 2020

Related U.S. Application Data

(62) Division of application No. 14/052,371, filed on Oct. 11, 2013, now Pat. No. 10,463,848.

(30) Foreign Application Priority Data

Oct. 12, 2012 (FR) ........................................ 1259758

(51) Int. Cl.
*A61N 1/05* (2006.01)
*A61B 5/24* (2021.01)
*A61N 1/372* (2006.01)

(52) U.S. Cl.
CPC .................. *A61N 1/05* (2013.01); *A61B 5/24* (2021.01); *A61N 1/056* (2013.01); *A61N 1/372* (2013.01);

(Continued)

(58) Field of Classification Search
CPC ................................. A61N 1/05; A61N 1/056
See application file for complete search history.

(56) References Cited

U.S. PATENT DOCUMENTS 1,691,869 A   11/1928 Fowle
2,320,470 A    6/1943 Rees
(Continued)

FOREIGN PATENT DOCUMENTS

CN   102333561       1/2012
EP   2 384 784 A1   11/2011
EP   2 455 131 A1    5/2012

OTHER PUBLICATIONS

Chinese Office Action for Patent Application No. 201310475838.1, dated Jan. 25, 2017, 14 pages.

(Continued)

*Primary Examiner* — Rex R Holmes
*Assistant Examiner* — Jennifer L Ghand

(57) ABSTRACT

Leads for use with implantable medical devices may be implanted in the venous, arterial, or lymphatic networks. The diameter of a microlead may be at most equal to 1.5 French (0.5 mm), and it may include a plurality of microcables each including: an electrically conductive core cable for connection to one pole of a multipolar generator of an active implantable medical device, and a polymer insulation layer surrounding the core cable. At least one exposed area may be formed in the insulation layer to form a detection/stimulation electrode.

17 Claims, 5 Drawing Sheets

(52) U.S. Cl.
CPC . *A61N 2001/0585* (2013.01); *Y10T 29/49224* (2015.01)

(56) References Cited

U.S. PATENT DOCUMENTS

| | | | |
|---|---|---|---|
| 4,640,393 | A | 2/1987 | Nishimura et al. |
| 4,945,341 | A | 7/1990 | Buttimer |
| 4,945,342 | A | 7/1990 | Steinemann |
| 4,964,414 | A | 10/1990 | Handa et al. |
| 5,246,014 | A | 9/1993 | Williams et al. |
| 5,760,341 | A | 6/1998 | Laske et al. |
| 6,192,280 | B1 | 2/2001 | Sommer et al. |
| 6,321,102 | B1 | 11/2001 | Spehr et al. |
| 7,047,082 | B1 | 5/2006 | Schrom et al. |
| 7,138,582 | B2 | 11/2006 | Lessar et al. |
| 7,155,294 | B2 | 12/2006 | Alinder |
| 7,287,366 | B2 | 10/2007 | Dye et al. |
| 2003/0236562 | A1 | 12/2003 | Kuzma |
| 2006/0106443 | A1 | 5/2006 | Michael et al. |
| 2008/0046059 | A1* | 2/2008 | Zarembo ............... A61N 1/057 607/122 |
| 2008/0114230 | A1 | 5/2008 | Addis |
| 2009/0076579 | A1* | 3/2009 | Boser .................... A61N 1/05 607/122 |
| 2009/0157136 | A1 | 6/2009 | Yang et al. |
| 2010/0077606 | A1* | 4/2010 | Black ................... A61N 1/056 29/825 |
| 2010/0137928 | A1 | 6/2010 | Duncan et al. |
| 2010/0222860 | A1 | 9/2010 | Casella et al. |
| 2011/0137382 | A1 | 6/2011 | Swanson |
| 2011/0220408 | A1 | 9/2011 | Walsh et al. |
| 2012/0130464 | A1 | 5/2012 | Ollivier |
| 2012/0271369 | A1* | 10/2012 | Ollivier ................ A61N 1/059 607/4 |
| 2013/0053864 | A1* | 2/2013 | Geroy .................... A61N 1/05 606/129 |

OTHER PUBLICATIONS

Chinese Office Action for Patent Application No. 2013104758381 dated Sep. 25, 2017, 16 pages.
Preliminary French Search Report for French Patent Application No. 1259758, dated Feb. 20, 2013, 2 pages.

* cited by examiner

IMPLANTABLE DETECTION/STIMULATION MULTIPOLOR MICROLEAD

CROSS-REFERENCE TO RELATED APPLICATIONS

This application is a divisional application of U.S. patent application Ser. No. 14/052,371, filed Oct. 11, 2013, which claims the benefit of and priority to French Patent Application No. 1259758, filed Oct. 12, 2012, both of which are incorporated herein by reference in their entirety.

BACKGROUND

The disclosure generally relates to the "active implantable medical devices" as defined by Directive 90/385/EEC of 20 Jun. 1990 of the Council of the European Communities.

This definition includes in particular cardiac implants for monitoring of the cardiac activity and for the generation of stimulation, defibrillation and/or resynchronization pulses, in case of arrhythmia detected by the device, and/or for sensing electrical activity. It also includes neurological devices, cochlear implants, medical substance diffusion pumps, implantable biological sensors, etc.

These devices may comprise a housing generally designated as a "generator", electrically and mechanically connected to one or more intracorporeal "leads" having electrodes for coming into contact with the tissue (e.g., myocardium, nerve, muscle, etc.) in which it is desirable to apply stimulation pulses and/or to collect an electrical signal.

According to some exemplary embodiments, the present disclosure more specifically relates to a detection/stimulation microlead for implantation in the venous, arterial or lymphatic systems.

The current principle of electrical stimulation of tissues is based on a device, usually called a "lead", which is an object notably implanted through various venous, arterial or lymphatic vessels, and the function of which is to transmit an electrical signal to the target tissue. The lead may be used to effectuate one or more of the following properties:

- Ease of implantation by the physician in a vessel network of the patient, and especially ease of advancing the lead into the vessels by pushing, making the lead follow tortuous branches and crossings, and transmitting torque;
- X-ray vision to allow the physician easy navigation through the vessels of the network under X-ray fluoroscopy;
- Atraumaticity of the lead in the veins, which requires a very flexible structure and the absence of rigid transition or sharp edges;
- Ability to transmit an electrical signal to the tissues and to stably perform monopolar or multipolar electrical measurements;
- Biocompatibility with living tissue for a long-term implantation;
- Ability to connect to an implantable device, source of signal transmission;
- Ability to sterilize (gamma rays, temperature, . . . ) without damage;
- Biostability, especially corrosion resistance in the living environment and resistance to mechanical stress fatigue related to patient and organs movement, and
- Compatibility with MRI imaging which is particularly important in neurology.

The current architecture of the leads meeting these requirements can be summarized in a generally hollow structure to allow passage of a stylet or a guidewire, and comprising components such as insulated conductor cables, connected to mechanical electrodes for providing electrical conductivity, radiopacity, etc.

These leads thus require a complex assembly of a large number of parts, wires and associated insulation, creating significant risk of breakage due to mechanical stresses to which they are exposed in the long term.

Examples of such leads are given in U.S. Pat. Nos. 6,192,280 A and 7,047,082 A.

Among the difficulties met, the management of stiffness gradients related to mechanical parts used, which strongly affect the implantability properties and mechanical strength over the long term (fatigue), can be cited. Furthermore, in terms of fatigue of assemblies, any stiffness transition zone may induce risks of fatigue, difficulty to sterilize due to the presence of zones difficult to access, and problems of solidity of the conductor junctions at the connection with the electrodes and the connector.

Moreover, the clinical trend in the field of implantable leads is to reduce the size to make them less invasive and easier to handle through the vessels. The current size of implantable leads is typically of the order of 4 to 6 Fr (1.33 to 2 mm).

However, it is clear that reducing the size of the leads increases complexity and imposes technical constraints generating risks.

SUMMARY

One embodiment of the disclosure relates to a sensing/pacing multipolar lead configured for implantation into a venous, arterial, or lymphatic network. The lead includes a plurality of microcables. Each microcable includes an electrically conducting core cable configured to be connected to a pole of a multipolar generator of an active implantable medical device. The core cable includes a plurality of elementary strands twisted together. The microcable further includes a polymer insulation layer surrounding the core cable. The polymer insulation layer has formed therein at least one exposed area. The core cable includes at least one bare core cable portion exposed through the at least one exposed area. The at least one bare core cable portion forms a monopolar detection/stimulation electrode. The plurality of microcables are coupled together in a twisted configuration within the lead and together form a multipolar detection/stimulation distal active portion of the lead.

Another embodiment relates to a lead for an implantable medical device. The lead includes a plurality of microcables. Each microcable includes a core cable including a plurality of cable strands and an insulation layer surrounding the core cable. The insulation layer has formed therein at least one exposed area, and the core cable includes at least one bare core cable portion exposed through the at least one exposed area. Each at least one bare core cable portion comprises an electrode usable by the implantable medical device to perform at least one of sensing and stimulation.

Yet another embodiment relates to an implantable medical device that includes a generator and a lead. The generator includes an electronic circuit configured to perform at least one of a sensing operation and a stimulation operation. The lead is configured to be connected to the generator and used by the generator in performing the at least one of the sensing operation and the stimulation operation. The lead includes a plurality of microcables. Each microcable includes a core cable including a plurality of strands and an insulation layer surrounding the core cable. The insulation layer has formed therein at least one exposed area, and the core cable includes at least one bare core cable portion exposed through the at least one exposed area. Each at least one bare core cable portion comprises an electrode of the lead.

Another embodiment relates to a method of forming a lead for use with an implantable medical device. The method includes providing a plurality of microcables. Each microcable includes a core cable and an insulation layer surrounding the core cable, and the core cable comprises a plurality of cable strands. The method further includes forming, for each of the plurality of microcables, at least one exposed area within the insulation layer and exposing at least one bare core cable portion through the at least one exposed area. Each at least one bare core cable portion forms an electrode of the lead.

Another exemplary embodiment relates to a sensing/pacing multipolar lead for implantation into a venous, arterial, and/or lymphatic network. The lead includes a plurality of microcables. Each microcable includes an electrically conducting core cable, for connection to one pole of a multipolar generator of an active implantable medical device, and a polymer insulation layer surrounding the core cable. The polymer insulation layer includes at least one exposed area formed in the insulation layer and forming a monopolar detection/stimulation electrode. Each core cable is formed by a plurality of elementary strands joined together in a respective strand of strands. The strand of strands of the different microcables are themselves assembled together in a strand of microcables. The strand of microcables forms a multi-polar detection/stimulation distal active portion of the lead. The lead is a microlead, the diameter of said distal active portion being at most equal to 1.5 French (0.5 mm).

In one or more of the above-identified embodiments:
- the lead may have an outer diameter less than or equal to 1.5 French;
- the distal ends of the microcables may be longitudinally shifted (l) from each other, so as to produce a progressive reduction of the diameter and to introduce a stiffness gradient in the most distal portion of the microlead;
- the lead may include a central microcable having a distal electrode;
- the core cable may be formed by a plurality of individual strands of 0.033 mm diameter;
- the core cable may have a diameter of 0.1 mm and may be formed by a strand of seven elementary strands of 0.033 mm diameter;
- the elementary strands may have a composite structure consisting of a structuring material and of a radiopaque material;
- in some embodiments, the structuring material is a stainless steel, a MP35N cobalt alloy, a precious metal, titanium, or a NiTi alloy;
- in some embodiments, the radiopaque material is tantalum (Ta), tungsten (W), iridium (Ir), platinum (Pt), or gold (Au);
- the elementary strands may include an outer layer of material of low magnetic susceptibility (e.g., lower than $2000 \times 10^{-12}$ $m^3 \times mol^{-1}$);
- in some embodiments, the material of low magnetic susceptibility is tantalum (Ta), titanium (Ti), rhodium (Rh), molybdenum (Mo), tungsten (W), palladium (Pd), or gold (Au);
- the insulation layer may have a thickness of 25 µm;
- the polymer constituting the insulation layer may be a fluoropolymer;
- the lead may include a sleeve of heat-shrinkable polymer partially surrounding the microlead;
- the detection/stimulation electrode may include a conductive ring fixed on a microcable exposed area by reduction of its outer diameter;
- the detection/stimulation electrode may include an inner conductive ring fixed on an exposed area by reduction of its outer diameter and an outer conductive ring fixed to the inner ring;
- the outer ring may be fixed to the inner ring by laser welding or bonding using a conductive adhesive;
- the detection/stimulation electrode may include a conductive ring attached to an exposed area by adhesive bonding using a conductive adhesive;
- the conductive rings may include platinum-iridium;
- the exposed area may extend 360 degrees over a length corresponding to one turn of microcable strand; and/or
- the lead may include a dipole including two 360 degree exposed areas disposed face-to-face on two non-consecutive microcables.

BRIEF DESCRIPTION OF THE DRAWINGS

Further features, characteristics and advantages of the present disclosure will become apparent to a person of ordinary skill in the art from the following detailed description of the present disclosure, made with reference to the drawings annexed, in which like reference characters refer to like elements and in which.

DETAILED DESCRIPTION

Figure 1:
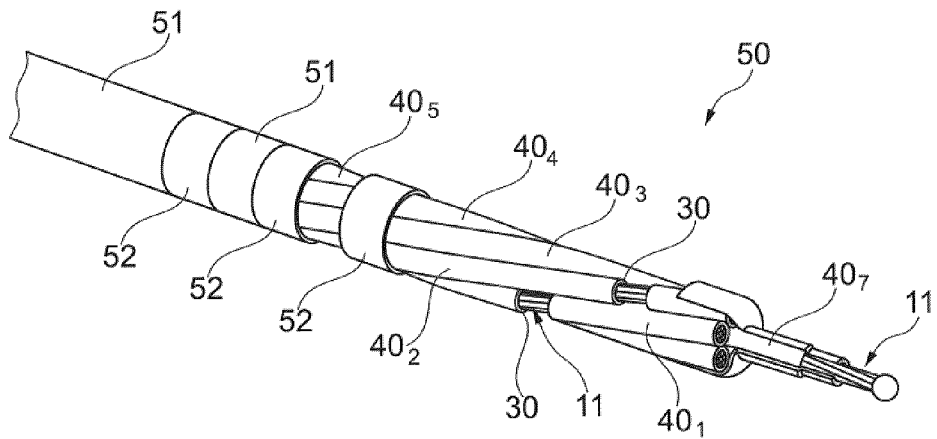
FIG. 1 is a partial perspective view of a detection/stimulation multipolar microlead according to an exemplary embodiment of the disclosure.

A reduction of lead diameter, to less than 1.5 French (0.5 mm), for example, may open up prospects for medical applications in various fields ranging from cardiology to neurology in the presence of a vein, artery or even lymphatic network such as the cerebral venous network or the coronary sinus venous network.

Today, the technology of electrical stimulation has led to major advances in the field of neuromodulation, which is to stimulate target areas of the brain for treatment of Parkinson's disease, epilepsy and other neurological diseases.

One could imagine what could be achieved with this type of technology to address new areas difficult to reach today, by small stimulation leads or "microleads", with great strength to ensure long-term biostability. With small microleads, it is possible to notably consider the passage of anastomosis to implant a stimulation device of the left ventricle via two distinct areas.

Such a technique would also allow a less invasive approach to these therapies and especially superior efficacy of treatments. It would also be possible to connect one or more microleads through the considered vessel network to the target location. Their implantation could be done, because of their small size, by guiding devices used in interventional neuroradiology today for the release of springs (coils) in the treatment of intracranial aneurysms. In particular, microleads of 1.5 French are compatible with catheters with an internal diameter of 1.6 French.

Furthermore, there is a need to propose multipolar leads related to the function of "electronic repositioning" in applications. This offers many possibilities for stimulation of tissue through the choices and the polarization of certain lines of conduction from among the number of lines included in the microlead. This technique allows programming of stimulation areas according to the therapy, a very interesting property, especially in neurology.

EP 2455131 A1 and its US counterpart US 2012/0130464 (Sorin CRM SAS) disclose a lead grouping a plurality of distinct monopolar microleads. The lead body that includes the microleads has a number of lateral openings along its length from which successively emerge respective microcables. Each of these microcables forms a monopolar line extending in a counterpart vessel of the coronary network, thereby stimulating through the same lead several vessels (each vessel being stimulated by a monopolar microcable), and thus covering a large area of the left ventricle. But considered separately, each of the microleads has only one electrical conductor, and, therefore, cannot be subjected to an electronic repositioning.

A purpose of this disclosure, according to at least some exemplary embodiments, is to provide a small microlead which would be consistent with the general properties of implantable leads as they were listed above. A microlead of the present disclosure may reduce complexity and, therefore, the final cost, and/or may allow a multipolar connection on a same microcable in order to independently polarize lines and stimulate tissue by means of electrodes disposed at different positions along the microlead.

The size of the microlead may make it possible to access very small veins inaccessible today with larger devices. The microlead may also greatly facilitate the navigability in venous, arterial and lymphatic networks due to its flexibility and small size.

In some embodiments, the microlead may be configured to meet a number of requirements.

In terms of reliability of the conductor/electrode mechanical and electrical connection, the requirements may include avoiding designs that could affect the immediate mechanical strength of the conductor by assemblies of electrical continuity components inserted between different portions of conductors. In some embodiments, it may be better to utilize a physically continuous conductor. Maximum sealing may help avoid exposing the conductors to body fluids.

In terms of performance, the requirements may include:
To give the microlead an outside diameter compatible with the size of targeted vessels;
To not alter the local flexibility of the microlead to maintain maximum maneuverability, including passage through the small veins;
To ensure isodiameter profile to allow passage within an implantable catheter, and veins; and
To facilitate and simplify the microlead/catheter assembly process.

According to various embodiments of the disclosure, multipolar detection/stimulation microleads intended for implantation in venous, arterial and lymphatic networks are provided.

As disclosed in EP 2455131 A1 above, the lead may include a plurality of microcables, each microcable including an electrically conductive core cable, for connection to a pole of a multipolar generator of an active implantable medical device active. The lead may also include an insulation polymer layer surrounding the core cable. At least one exposed area may be formed in the insulation layer and may form a sensing/pacing electrode. Each core cable may be formed by a plurality of elementary strands joined together in a respective strand of strands.

According to some embodiments, the lead of the disclosure is remarkable in that the different strands of microcables are themselves assembled together in a strand of microcables and form an active distal portion of the lead for multipolar stimulation. In some embodiments, the diameter of the distal active portion may be at most equal to 1.5 French (0.5 mm).

The microlead may have high flexibility, enabling its manipulation by the physician, especially during its implantation, when, for example, it is introduced it into vessel networks with high tortuosity and many branches. The microlead may avoid injuries that could occur with much more rigid leads that are incompatible with tissue.

According to one embodiment, the core cable is formed by a plurality of individual strands of a diameter of 0.033 mm. In particular, a core cable of 0.1 mm is formed by a strand of seven elementary strands of 0.033 mm diameter.

The choice of a stranded multiwire structure composed of very thin elementary strands to constitute the core cables increases their resistance to mechanical fatigue due to patient and organ movement, the flexion breaking limit of a wire being substantially inversely proportional to its diameter.

To enhance this important biostability property, it is advantageous that, in some embodiments, the individual strands have a composite structure consisting of a structuring material and of a radiopaque material. The structuring material may have a high intrinsic resistance to fatigue, such as a stainless steel, a cobalt alloy (e.g., MP35N), a precious metal, such as titanium or a NiTi alloy notably known under the name of nitinol, etc. To these metals responsible for ensuring the mechanical qualities of the core cable is added a radiopaque material to make the microlead visible to X-ray during its implantation by the physician. In some embodiments, the radiopaque material can be selected from the group consisting of: tantalum (Ta), tungsten (W), iridium (Ir), platinum (Pt) and gold (Au).

To make electrical contact with the tissues and transmit the detection/stimulation electrical signals, the core cables may be used to form the electrodes of the microlead by exposing areas in an insulation layer surrounding the cables.

In some embodiments, the insulation layer is a fluorinated polymer, for example ethylene tetrafluoroethylene (ETFE), and has a thickness of 25 μm.

According to some embodiments, the microlead includes a strand of microcables (e.g., seven microcables). In some embodiments, a heat-shrinkable polymer sheath, for example of polyester (PET), may partially surround the microlead.

To limit the heating of the core cable by skin effect during MRI imaging, the strands may include an outer layer of material of low magnetic susceptibility, below $2000 \times 10^{-12}$ $m^3 \times mol^{-1}$. The material having a low magnetic susceptibility may be, optionally, selected from the group comprising: tantalum (Ta), titanium (Ti), rhodium (Rh), molybdenum (Mo), tungsten (W), palladium (Pd) and gold (Au).

According to some embodiments, a detection/stimulation electrode includes a conductive ring attached to an exposed microcable area by reduction of its outer diameter.

To prevent stress on the ring, the sheaths and the strands, in some embodiments, a detection/stimulation electrode includes, first, an inner conductive ring secured to an exposed area by reduction of its outside diameter, and, second, an outer conductive ring fixed on the inner ring. The rings may include, for example, platinum-iridium. The outer ring may be fixed to the inner ring by laser welding or gluing using a conductive adhesive.

The invention also discloses a detection/stimulation electrode comprising a conductive ring secured to an exposed area by gluing using a conductive adhesive.

In some embodiments, the exposed area extends 360° over a length corresponding to a coil of a microcable strand. It may be possible to carry out on the microlead at least a dipole consisting of two exposed areas on 360° arranged opposite on two nonconsecutive microcables.

Finally, in some embodiments, the distal ends of the microcables are longitudinally offset relative to each other, so as to produce a progressive reduction of the diameter and introduce a stiffness gradient in the most distal portion of the microlead.

The microleads of the disclosure may be detection/stimulation multipolar microleads intended to be implanted in venous, arterial and lymphatic networks. The diameter of the microleads, in some embodiments, may not exceed 1.5 French (0.5 mm). They may be particularly suited to applications involving the function of electronic repositioning, mentioned above, which involves a plurality of separate and independent conduction lines, each connected to one pole of the generator of an implantable device. In some embodiments, the lines may each be connected to one pole generator via an IS-1 or IS-4 connector for a cardiac lead, or even a larger number of poles for a neurological lead.

Figure 2:
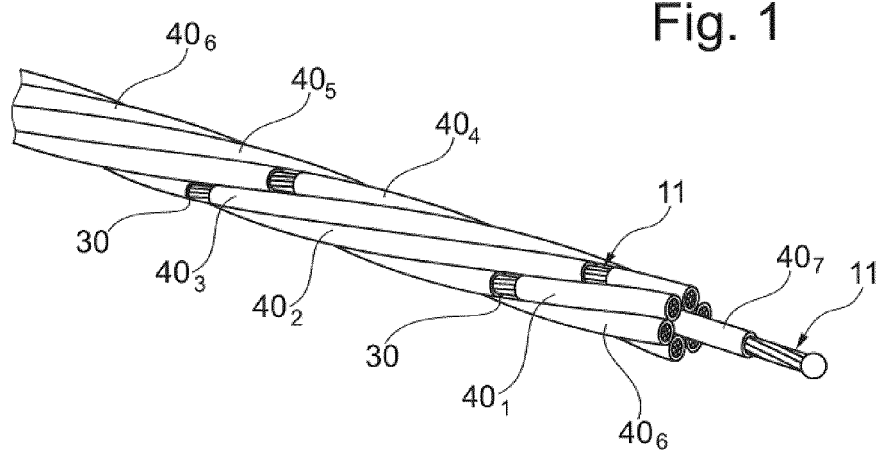
FIG. 2 shows the microlead of FIG. 1 before introduction of the outer sheath and the electrodes.

The microlead 50 shown in FIG. 1 includes seven microcables $40_1$, $40_2$, $40_3$, $40_4$, $40_5$, $40_6$, $40_7$ assembled in a strand as shown in FIG. 2. Each microcable forms for the microlead 50 a conduction line connected to a pole of the generator.

Figure 3:
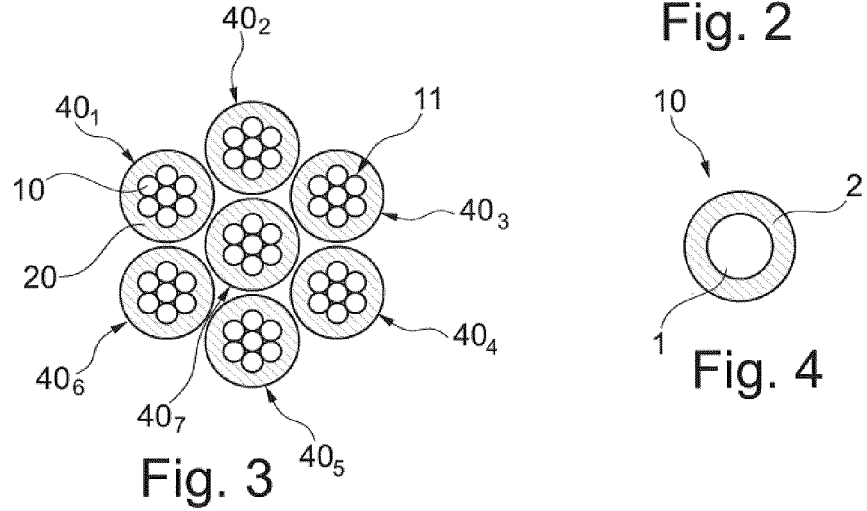
FIG. 3 is a cross section of the view of FIG. 2.

As shown in FIG. 3, a microcable comprises a core cable 11 surrounded by an insulation layer 20 that provides electrical insulation between the microcables.

In the embodiment shown in cross section in FIG. 3, each core cable 11 is formed by a strand of seven elementary wires 10 whose diameter is, for example, 0.033 mm. The diameter of a core cable 11 is then 0.1 mm.

Figure 4:
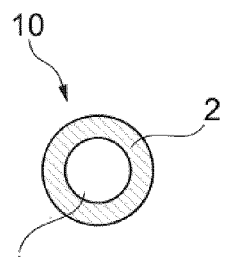
FIG. 4 is a sectional view of an elementary strand of a microcable shown in FIG. 3.

In some embodiments, elementary strands 10 of the type shown in FIG. 4 may be utilized. Such strands may include a core 1 of structural material such as stainless steel, an alloy of cobalt of the MP35N series, a noble metal, titanium, or a NiTi alloy, of high fatigue resistance. Such a core of structural material (e.g., having a diameter of 0.033 mm) may help achieve maximum tensile strength in the extreme fatigue stress conditions to which such structures can be submitted.

To ensure sufficient visibility to X-rays for the implantation of the microlead, it may be useful to introduce along the core cable a minimal amount of radiopaque material 2. Such a composite structure may exhibit both fatigue resistance and radiopacity. Materials that may be used for radiopaque material 2 may include materials known for visibility to X-rays, for example, tantalum (Ta), tungsten (W), iridium (Ir), platinum (Pt) and gold (Au). Such materials may generally not have high fatigue strength.

The compatibility of implantable devices with modern medical imaging techniques such as MRI, is essential to ensure optimal patient care.

Because of its overall metal structure, the microlead is at risk of overheating due to "skin effect" induced currents outside the elementary strands under the action of applied magnetic fields. However, due to the small diameter of the strands, heat dissipation is favored and the heating effects of MRI are reduced. Furthermore, the thermal energy stored by the material, already limited in volume, can be further reduced if the individual strands are coated with an outer layer of material of low magnetic susceptibility (magnetic susceptibility being the ability of a material to be magnetized by the action of an external magnetic field).

In some embodiments, favorable materials may include those whose magnetic susceptibility is less than $2000 \times 10^{-12}$ $m^3 \times mol^{-1}$, such as tantalum (Ta), titanium (Ti), rhodium (Rh), molybdenum (Mo), tungsten (W), palladium (Pd), and gold (Au).

In some embodiments, the thickness of the insulation layer 20 is 0.025 mm (25 μm). Microcables of a diameter equal to 0.150 mm and a strand of seven microcables of a diameter equal to 0.45 mm may be thus produced.

In various embodiments, characteristics required for the insulation layer 20 may include:
Fatigue resistance,
Electrical insulation,
Long-term biocompatibility,
Biostability
Possibility of transformation and implementation compatible with the conductor of the core cable.

To realize the insulation layer 20, materials with high chemical inertness, such as fluoropolymers, which also have very good insulation properties, may be preferred. Among these compounds, ETFE (ethylene tetrafluoroethylene) may in particular be mentioned.

Methods for producing the insulation layer 20 of the core cable are, for example, co-extrusion of the conductor or heating of a heat shrinkable tube.

As can be seen in FIGS. 1 and 2, in some exemplary embodiments, the insulation layers 20 surrounding the core cables 11 of the microcables have at least one exposed zone 30 to form a sensing/pacing electrode for the microlead 50, such as the electrodes 52 of FIG. 1. Such an exposed zone 30 may be formed according to manufacturing methods which will be described in greater detail below. The exposed zones 30 are obtained by techniques such as laser ablation.

In the case of stimulation in an anastomosis, for example, it is easily possible to add one or more series of electrodes on each microcable, in order to increase the number of stimulation points:

With one electrode per peripheral microcable, six peripheral electrodes of the central microcable and one electrode at its distal end are obtained, or seven poles and seven electrodes;

With two electrodes perperipheral microcable, twelve peripheral electrodes of the central microcable and one electrode at its distal end are obtained, or seven poles and thirteen electrodes;

With three electrodes per peripheral microcable, eighteen peripheral electrodes of the central microcable and one electrode at its distal end are obtained, or seven poles and nineteen electrodes; and so on.

This example takes into account only one distal electrode at the end of the central microcable $40_7$. It is, however, possible to place a plurality of electrodes if the microcable is elongated in its distal portion. In this case, there is no limit to the number of electrodes. For a microlead consisting of seven stranded microcables, the number of poles depends on the number of microcables, in the present example, seven poles.

Another possibility is to electrically connect a plurality of microcables to the same electrical potential to increase reliability by this redundancy.

It is thus possible, for example, with a 7×7 structure as illustrated in FIG. 3, to connect two (or three) of the seven microcables to the same pole of the proximal side of the generator. On the distal side, the electrodes of these microcables may be regrouped in the same stimulation zone to form a specific stimulation point. Conversely, the electrodes may be moved several centimeters from each other to create a large stimulation surface.

Finally, FIG. 1 more particularly shows that the microlead 50 is surrounded by an outer sheath 51, except in areas occupied by the electrodes 52. This sheath 51 may be of heat shrinkable polymer, such as polyethylene terephthalate (PET). In some embodiments, its thickness may be 0.025 mm (25 μm), which corresponds to a final diameter of 0.5 mm or 1.5 French for the microlead 50.

Figure 5:
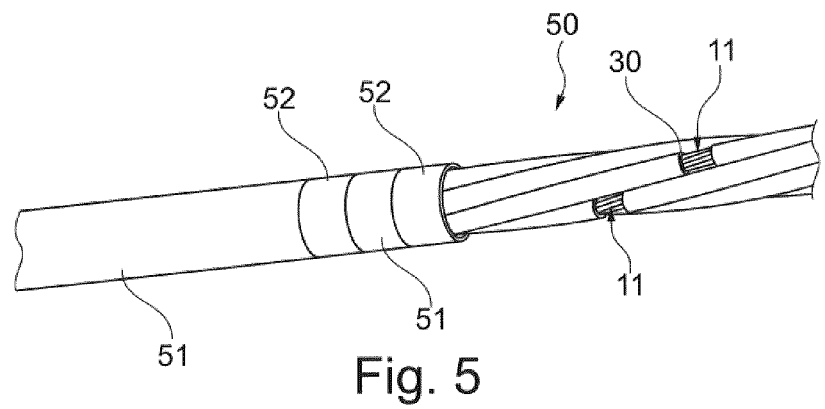
FIG. 5 is a partial perspective view of a microlead realized according to a first embodiment of the disclosure.

FIG. 5 illustrates a first embodiment of the microlead 50 in which the conductive rings 52 of platinum/iridium 90/10 are respectively placed next to a exposed area (not shown in the figure). Each ring 52 is fixed by reducing its outer diameter, for example by crimping, ensuring the local contact of the inner diameter of the ring 52 with the core cable 11 of the exposed microcable.

Reducing the diameter of the ring 52, obtained by deformation of material, results in stresses inherent to the ring but also to the insulation layer 20 and to the core cables 11. The material of the rings 52 may be sufficiently malleable to avoid damaging the nonexposed areas.

One method for assembly of the microlead 50 of FIG. 5 is to alternatively thread a shrink tubing length 51 and then a conductive ring 52.

It should be noted that the electrodes 52 are annular electrodes and allow 360° stimulation.

FIGS. 6a to 8c disclose variants configured to ensure the integrity of the different insulation layers during the implantation of the electrode 52.

Figure 6A:
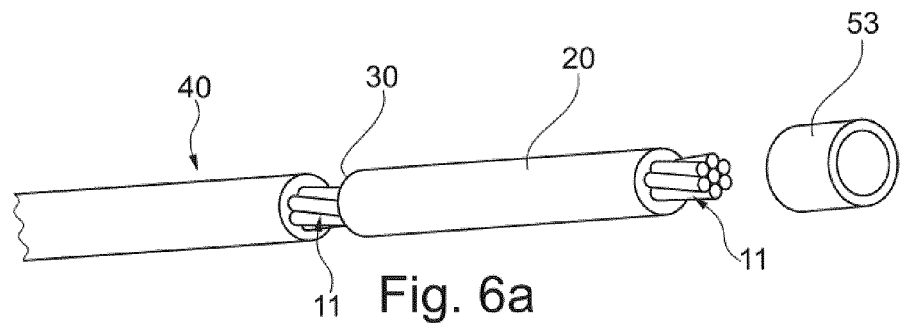
FIGS. 6a to 6c are views illustrating the steps of introducing an inner ring on a microcable according to a second embodiment.
Figure 6B:
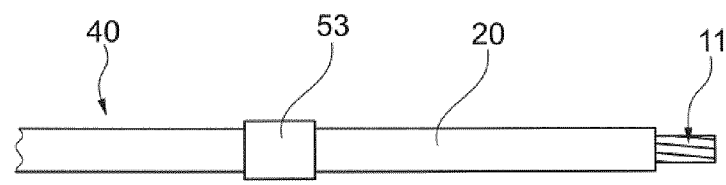
Figure 6C:
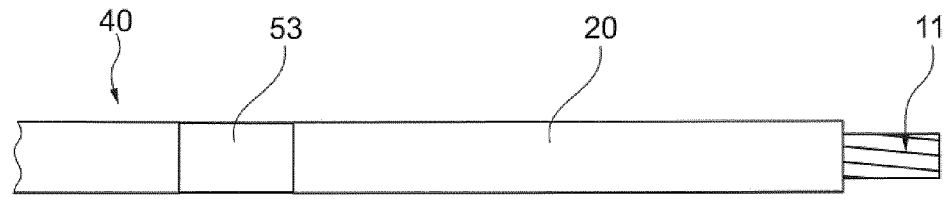

In the embodiment of FIGS. 6a to 7c, a first ring 53 may be threaded onto one of the microcables 40 (FIG. 6a) to be positioned facing an exposed area 30 (FIG. 6b). The inner ring may also include platinum-iridium, and/or may have an inner diameter at least equal to the outer diameter of the microcable (e.g., 0.15 mm) and/or an external diameter of 0.18 mm. The first ring 53 may be crimped (FIG. 6c) so as to make electrical contact with the core cable 11 and keep the isodiameter. The outer diameter of the inner ring 53 may be 0.15 mm.

This ring 53 may be used as the visible marker (FIG. 7a) under binocular, in vertical position for the positioning (FIG. 7b) of a second ring 52 (e.g., an outer ring or stimulation ring fixed to the inner ring 53).

This solution avoids subjecting the seven microcables to a crimping force. The electrical contact is then transferred between the two rings 52, 53. The risks of damage by crimping on the insulation layers 20 of the microcables are thus reduced.

A hole $52_1$ is formed in the outer ring 52 (FIG. 7c) to facilitate the orientation and positioning of rings 52, 53 for an assembly by laser welding.

Figure 8A:
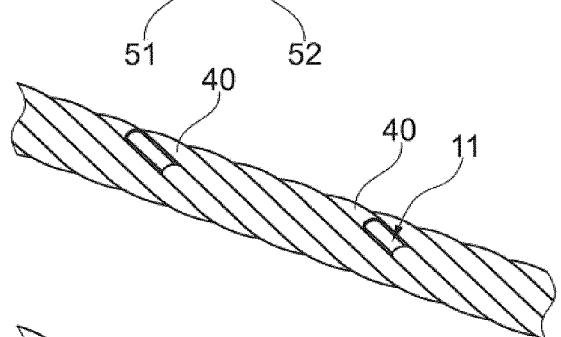
FIGS. 8a-8c are views illustrating the steps of gluing an outer ring on an exposed area of a microcable.
Figure 8B:
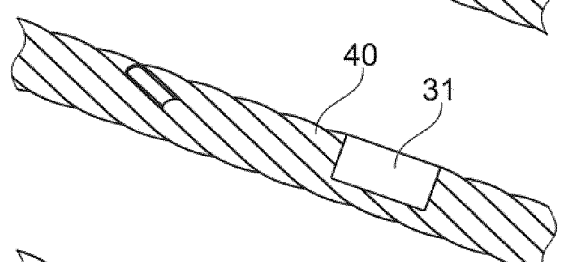
Figure 8C:
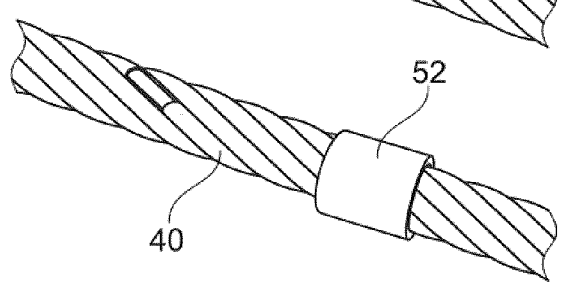

According to the embodiment of FIGS. 8a-8c, a particular microcable 40 has a zone 30 without insulation layer 20 (FIG. 8a). This exposed area is covered by a deposit of conductive adhesive 31 (FIG. 8b) for mounting and positioning an outer ring 52, which is the stimulation electrode, in contact with the tissues (FIG. 8c).

The function of the conductive adhesive is to transmit an electrical current between the two conductor components and to preserve the integrity of the insulation layers of the adjacent microcables. There is no risk of melting of the polymer of the insulation layers, or to cut them or locally reduce their thickness.

A wide range of biocompatible adhesives commonly used in implantable medical devices are available from Epoxy Technology, Inc.

Figure 7A:
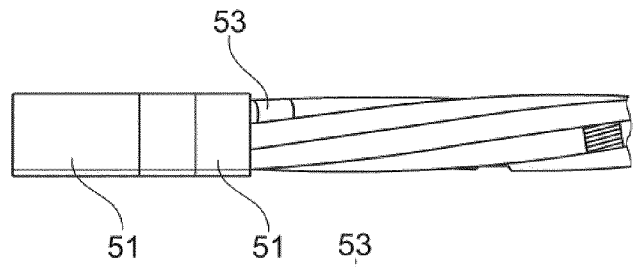
FIGS. 7a-7c are views illustrating the steps of attaching by laser welding an outer ring on the inner ring of FIGS. 6a to 6c.
Figure 7B:
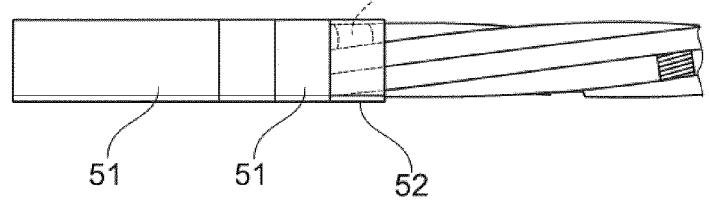
Figure 7C:
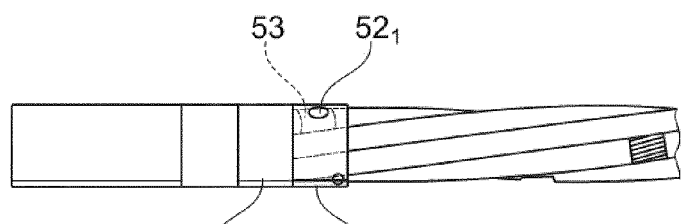

This gluing technique can also be applied to the assembly of an inner ring 53 and an outer ring 52, as described with reference to FIGS. 7a-7c.

The structure beneath the glued rings consists of rigid and non-compressible metal strands and of insulating layers of soft, and therefore compressible, polymer. On a microscopic scale, it is possible to define this structure as flexible and possibly varying in size and geometry. The use of glue is to compensate these microscopic deformations due to the intrinsic characteristics of the glue and to introduce a relative flexibility in the assembly of the two rings and make this attachment less brittle when subjected to tensile, bending or torsion stresses.

Figure 9:
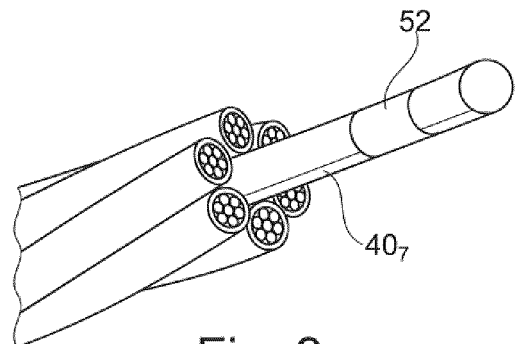
FIG. 9 is a partial perspective view showing an electrode in the distal portion of the central microcable of the microlead of FIG. 1.

FIG. 9 shows a distal electrode 52 arranged at the end of the central microcable $40_7$ and manufactured according to one of the preceding embodiments, including the one involving an inner ring and an outer ring.

Figure 10:
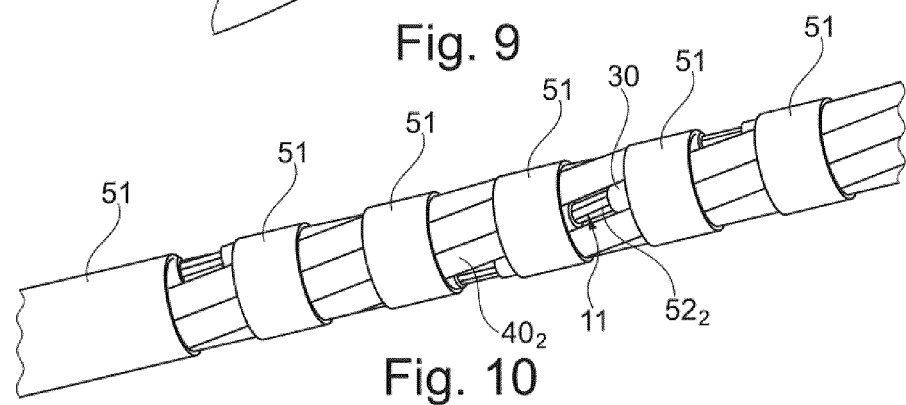
FIG. 10 is a partial perspective view of a microlead realized according to a third embodiment.

FIG. 10 shows a version of the multipolar microlead wherein the electrodes are directly formed by the elements of core cables 11. For example, the electrode $52_2$ in FIG. 10 is the portion of the core cable 11 exposed through the exposed area 30 of the microcable $40_2$. In this case, each individual strand being a conductor, its material is biocompatible, e.g. core 1 of MP35 and envelope 2 of platinum.

The strength of the structure is ensured by an alternation of elements of sheath 51 surrounding the strand of seven microcables. Preferably, the length in the alternation of the outer sheath is greater than the lengths of the intervals. This sheath also plays an important role in the handling of the microlead, during insertion into the catheter. It also provides the shaping of the distal portion to reduce the risk of movement of the microlead in the veins.

It should be noted that in this configuration, each point of stimulation is angularly oriented and does not allow annular stimulation.

The electrode surface area is about 0.314 mm² for a length of 1 mm. This small stimulation area is favorable to the longevity of the battery.

Figure 11A:
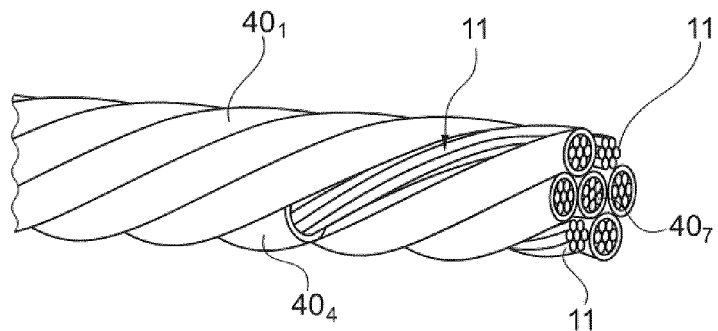
FIGS. 11a and 11b are views showing the realization of a dipole on a microlead in accordance with an exemplary embodiment of the disclosure.
Figure 11B:
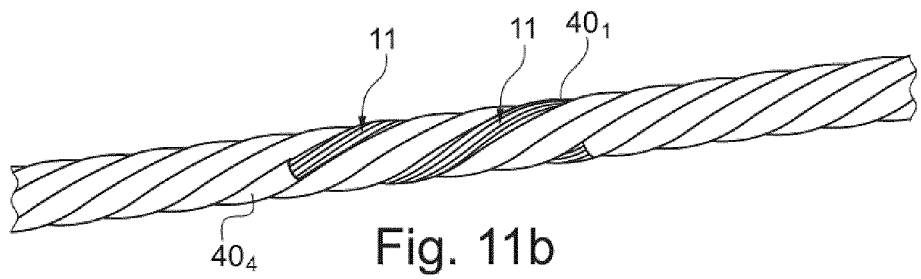

FIGS. 11a and 11b show a low power dipole consisting of spiral microcables and each covered, in this case, with a heat-shrink PET sheath. For the two microcables $40_1$ and $40_4$, first an exposed area 30 of a length corresponding to one turn (360°) is made, thereby increasing the conductive surface of each core cable 11 to a value equivalent to that of an annular ring electrode.

The conductive surface thus twisted provides better contact with the tissues of the vein on 360°.

This architecture allows the manufacturing of a microlead that can be used as a dipole and thus get a very small distance between the poles. In this example, the distance between the poles is 0.15 mm, separated by a central microcable $40_7$ of constant thickness.

The position of the two exposed microcables in the periphery may notably differ by alternation of nonconsecutive microcables, such as wrapped microcable/exposed microcable.

The advantage of such a device is to create an electric field between two electrodes, at a very short distance, of the same surface, of the same material, and located in the same electrolyte, which has the effect of increasing the intensity of the electric field.

Figure 12A:
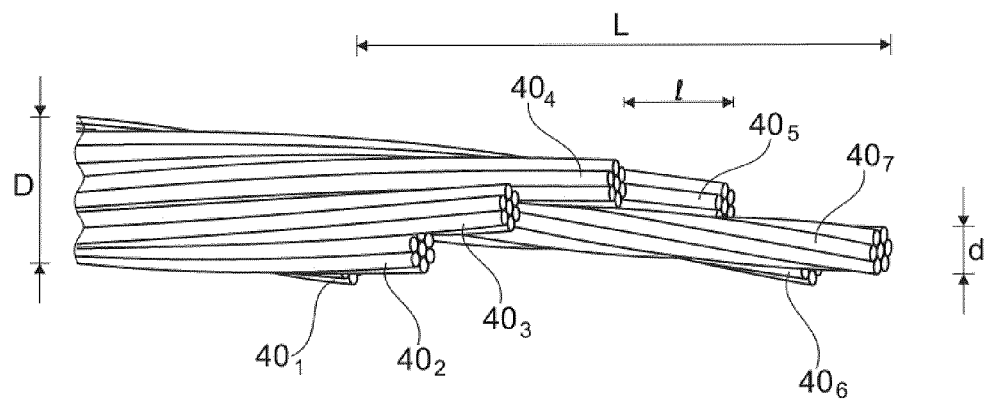
FIGS. 12a and 12b illustrate an improvement of the embodiments described in the preceding figures, achieving a gradual reduction in diameter in the distal end of the lead.
Figure 12B:
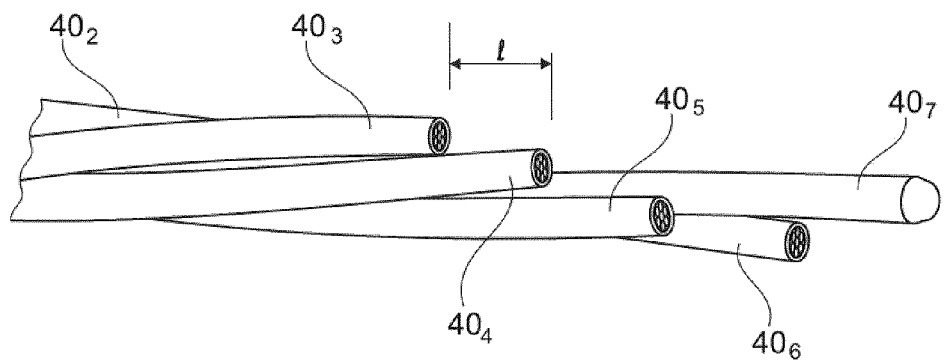

FIGS. 12a and 12b illustrate an improvement of the embodiments described above, by shifting each end of the strand (and thus of the microcable) e.g. l=1 to 5 mm from the end of the previous strand. The result is a gradual decrease in the diameter of the end of the microlead, which, in this example, gradually changes from D=0.45 to d=0.15 mm, on a length of L=20 to 30 mm.

This longitudinal offset of the ends of the individual strands has two advantages:
  First, it introduces in the most distal part of the microlead a stiffness gradient avoiding an abrupt change in diameter between the beam combining all microcables $40_1$-$40_7$ and the central microcable $40_7$, which greatly reduces the risk of premature failure of components due to bending mechanical stresses;
  Second, it improves the electrical insulation between the strands, and therefore the insulation of the different poles of the microlead, while avoiding any immediate vicinity of non insulated ends of the conductor cores of the different microcables.

What is claimed is:

1. A method of forming a lead for use with an implantable medical device, the method comprising:
  providing a plurality of microcables, each microcable comprising a core cable and an insulation layer surrounding the core cable, wherein the core cable comprises a plurality of cable strands; and
  forming, for each of the plurality of microcables, at least one exposed area within the insulation layer and exposing at least one bare core cable portion through the at least one exposed area, wherein the at least one exposed area within the insulation layer is formed between a first heat-shrinkable polymer sheath of the insulation layer and a second heat-shrinkable polymer sheath of the insulation layer;
  wherein each at least one bare core cable portion forms an electrode of the lead, wherein the lead has an outer diameter of no greater than 1.5 French.

2. The method of claim 1, further comprising longitudinally shifting distal ends of the plurality of microcables from each other to produce a progressive reduction of the diameter and to introduce a stiffness gradient in a distal portion of the lead.

3. The method of claim 1, further comprising positioning a central microcable in a center of the plurality of microcables, the center microcable having a distal electrode.

4. The method of claim 1, further comprising forming, for each of the plurality of microcables, the core cable by twisting a plurality of elementary strands together.

5. The method of claim 4, further comprising forming the elementary strands from a composite structure comprising a structuring material and a radiopaque material.

6. The method of claim 4, further comprising forming an outer layer of the elementary strands from a material of low magnetic susceptibility, wherein the magnetic susceptibility of the outer layer of material is lower than $2000 \times 10^{-12} m^3 \times mol^{-1}$.

7. The method of claim 1, wherein the insulation layer comprises a fluoropolymer.

8. The method of claim 1, further comprising coupling together the plurality of microcables in a twisted configuration within the lead such that the twisted configuration includes a center microcable and a plurality of peripheral microcables surrounding the center microcable and forming a multipolar detection/stimulation distal active portion of the lead.

9. The method of claim 8, further comprising extending the at least one exposed area 360 degrees around a circumference of the lead over a length corresponding to one turn of the microcable within the twisted configuration.

10. The method of claim 9, further comprising forming a dipole with two non-consecutive microcables of the plurality of microcables, such that an exposed area of each of the two microcables extends 360 degrees around the circumference of the lead and the exposed areas of the two non-consecutive microcables are disposed across from one another within the twisted configuration.

11. The method of claim 1, further comprising positioning an inner ring on each of the at least one bare core cable portion of each of the plurality of microcables.

12. The method of claim 11, further comprising positioning an outer ring to surround the plurality of microcables, wherein the outer ring is in electrical contact with the inner ring.

13. The method of claim 1, wherein each of the plurality of microcables is configured to be individually conductive and individually-selectable by an implantable medical device, for selective stimulation of the separately exposed areas.

14. A lead for an active implantable medical device formed by a process comprising the steps of:
  providing a plurality of microcables, each microcable comprising a core cable and an insulation layer surrounding the core cable, wherein the core cable comprises a plurality of cable strands; and
  forming, for each of the plurality of microcables, at least one exposed area within the insulation layer and exposing at least one bare core cable portion through the at least one exposed area, wherein the at least one exposed area within the insulation layer is formed between a first heat-shrinkable polymer sheath of the insulation layer and a second heat-shrinkable polymer sheath of the insulation layer;
  wherein each at least one bare core cable portion forms an electrode of the lead, wherein the lead has an outer diameter of no greater than 1.5 French.

15. The lead of claim 14, wherein the process of forming the lead further comprises longitudinally shifting distal ends of the plurality of microcables from each other to produce a progressive reduction of the diameter and to introduce a stiffness gradient in a distal portion of the lead.

16. The lead of claim 14, wherein the process of forming the lead further comprises coupling together the plurality of microcables in a twisted configuration within the lead such that the twisted configuration includes a center microcable and a plurality of peripheral microcables surrounding the center microcable and forming a multipolar detection/stimulation distal active portion of the lead.

17. The lead of claim 14, wherein each of the plurality of microcables is configured to be individually conductive and individually-selectable by an implantable medical device, for selective stimulation of the separately exposed areas.

* * * * *